United States Patent [19]

Shek et al.

[11] Patent Number: 4,938,965

[45] Date of Patent: Jul. 3, 1990

[54] OCULAR DELIVERY OF PROPHYLACTIC AGENTS

[75] Inventors: Pang N. Shek, Willowdale; Raymond F. Barber, Toronto, both of Canada

[73] Assignee: Her Majesty the Queen in right of Canada, as represented by the Minister of National Defence of Her Majesty's Canadian Government, Ottawa, Canada

[21] Appl. No.: 76,449

[22] Filed: Jul. 22, 1987

[51] Int. Cl.[5] ...................... A61K 9/127; A61K 37/20
[52] U.S. Cl. ...................................... 424/450; 514/78; 514/912; 514/913; 514/914; 514/915
[58] Field of Search ................ 424/450; 514/912, 913, 514/914, 915, 78

[56] References Cited

U.S. PATENT DOCUMENTS

| | | | |
|---|---|---|---|
| 4,239,754 | 12/1980 | Sache et al. | 514/78 |
| 4,460,577 | 7/1984 | Moro et al. | 424/450 |
| 4,485,054 | 11/1984 | Mezei et al. | 424/450 |
| 4,649,047 | 3/1987 | Kaswan | 514/912 |
| 4,753,945 | 6/1988 | Gilbard et al. | 424/450 |

*Primary Examiner*—Mark L. Bell
*Assistant Examiner*—Anthony J. Green
*Attorney, Agent, or Firm*—Nixon & Vanderhye

[57] ABSTRACT

The invention disclosed is a composition and method for the slow sustained ocular delivery of a prophylactic agent contained in liposome vesicles. The liposome vesicles are composed of phospholipid and cholesterol in a molar ratio of phospholipid to cholesterol of 8:2 to 1:1. Preferably, stearylamine is included in the liposome composition.

14 Claims, 3 Drawing Sheets

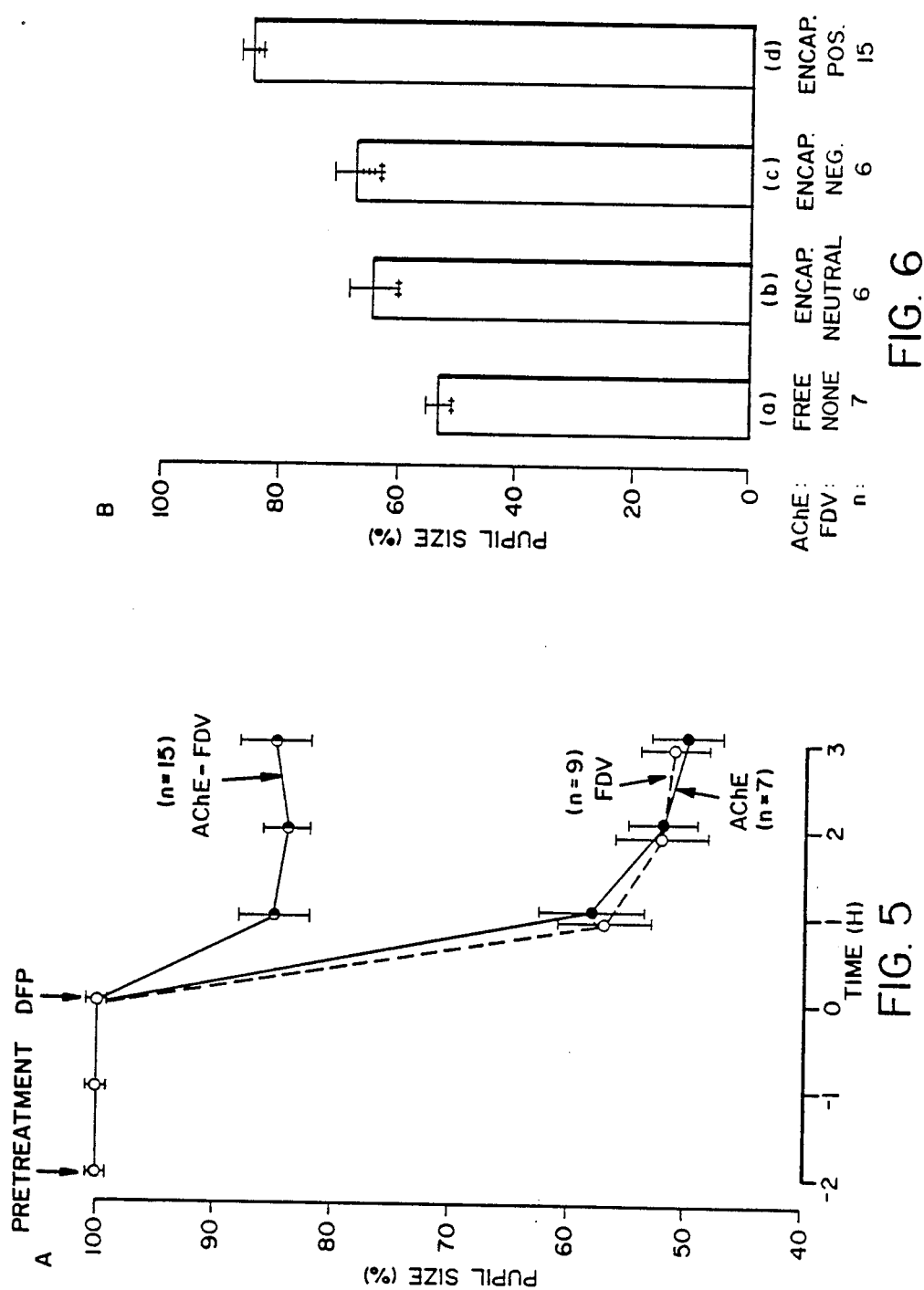

OCULAR DELIVERY OF PROPHYLACTIC AGENTS

This invention relates to liposomes, and in particular to the use of liposomes as a topical ophthalmic delivery device for prophylactic agents.

Liposomes are phospholipid vesicles which have been shown to be biodegradable and relatively non-toxic. These lipid vesicles can be used for the entrapment of hydrophilic and hydrophobic substances including drugs, enzymes, antigens, hemoglobins, and a whole host of other biologically active materials.

Liposomes, as potential carriers of drugs and biologicals, have stimulated considerable interest as delivery devices both in vivo and in vitro. One of the major obstacles encountered in the application of liposome technology for in vivo drug delivery via the circulatory route has been the removal or destruction of the liposome before any benefit can be achieved. Liposomes injected into the circulatory system are generally taken up rapidly by cells of the reticuloendothelial system and, even before phagocytosis, serum components act to disrupt liposome integrity. This results in the premature loss of associated agents. Resistance to in vivo degradation has been variously accomplished through the inclusion of cholesterol, saturated phospholipids, sphingolipids, and glycolipids.

Even though liposomal drug delivery within the body has received considerable attention, successes have been limited. While much of the reason for this lack of success stems from the problems outlined above, the impenetrability of most of the vascular endothelium generally prohibits extravascular movement of liposomes injected into the blood-stream. For these reasons, effective liposome-mediated delivery has been most successful when the preparations are delivered directly to the anatomical site where an effect is desired.

Conventional eye drops cannot provide sustained therapeutic drug levels in the precorneal area. Drug delivery by this method is pulsed with an initial high drug level followed by dilution and removal by normal lacrimation.

Similarly, when liposomes are employed as carriers for ocular drug delivery, it has been found that the presence of tear fluid in the eyes increases the release of drugs.

Cholesterol has been employed in liposome compositions by Christopher J. Kirby et al in Liposome Technology, Vol. 1, 19-27, CRC Press, Boca Raton, Fla., 1984 to enhance entrapment of prophylactic agents. Specifically, Kirby et al found that entrapment of a selective agent was enhanced by employing equimolar amounts of phospholipid and cholesterol. In one specific example, stearylamine was included to impart a positive charge. It is interesting to note that in that example, employing equimolar amounts of phospholipid and cholesterol, a lower level of entrapment of agent was observed.

According to the invention, a liposome compositon for slow sustained ocular delivery of a prophylactic agent is provided comprising phospholipid and cholesterol in a molar ratio of phospholipid to cholesterol of 8:2 to 1:1. Preferably, stearyl amine is included in the compositon, wherein the molar ratio of phospholipid to cholesterol to stearylamine is 4.5–9:0.5–4.5:1.

According to another aspect of the invention, a method for the slow sustained ocular delivery of a prophylactic agent is provided. The prophylactic agent is contained in a liposome composed of phospholipid and cholesterol in a molar ratio of phospholipid to cholesterol of 8:2 to 1:1. A specific prophylactic enzyme, acetylcholinesterase is employed by applicant in counteracting the miotic effect of diisopropylfluorophosphate (DFP), a prototype of a family of organophosphate poisons found in insecticides and chemical nerve agents. The potential exposure of these and other toxic agents to the eye is a serious occupational hazard for some professional groups, e.g. insecticide workers and some military personnel. Our studies demonstrate that the enzyme-liposome complex may act somewhat like a sponge by sequestering DFP molecules which diffuse into the vesicle and also by releasing the entrapped enzyme to combine with DFP, thereby neutralizing its toxic effect.

In the drawing which illustrates the embodiments of the invention,

FIG. 5 is a graph which illustrates the effect of a prophylactic agent delivered from a multilamellar liposome according to the invention; and FIG. 6 is a graph illustrating the effect of positive charge on prophylactic effect.

Figure 1:
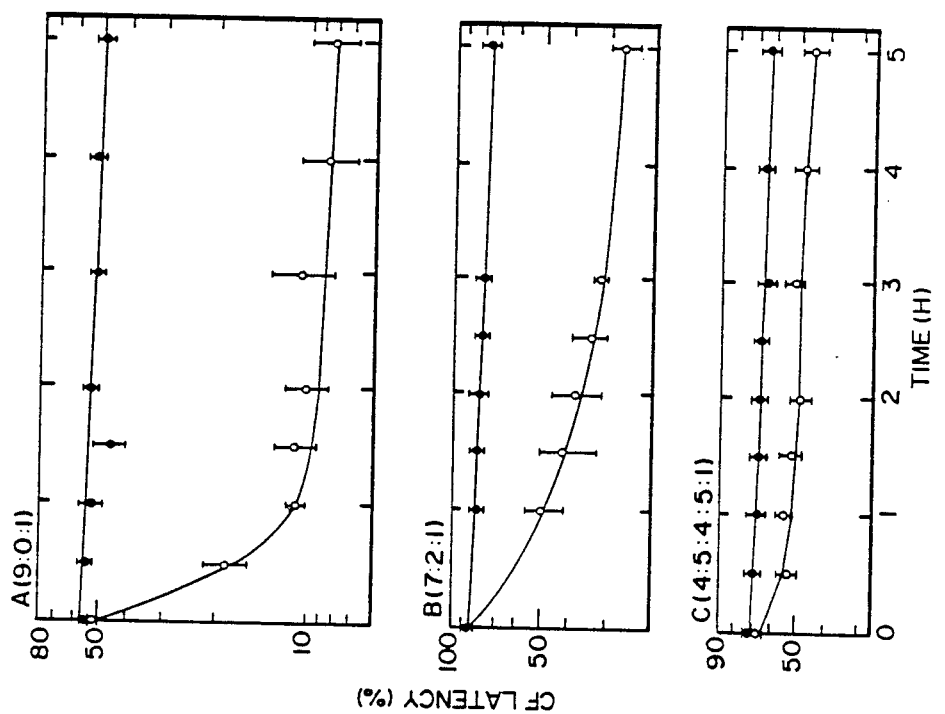
FIG. 1 is a graph illustrating the effect of rabbit tear fluid on marker dye release from unilamellar liposomes.

More specifically, in FIG. 1, the liposomes were prepared from egg phosphatidylcholine, cholesterol and stearylamine in molar ratios of 9:0:1 (A), 7:2:1 (B) and 4.5:4.5:1 (C). The vesicles were incubated at 37° C. in equal volume of either buffer (●) or tear fluid (○). Latency values are means ± S.E. from at least three independent experiments.

Figure 2:
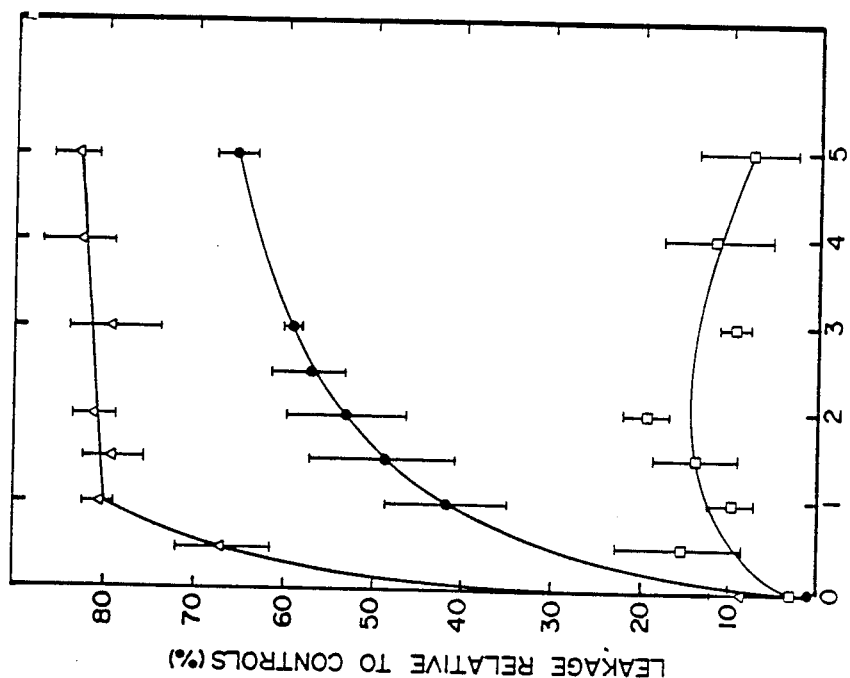
FIG. 2 is a graph which illustrates the effect of liposomal cholesterol content on tear-induced dye release.

In FIG. 2, liposomes were prepared with molar ratios of 9:0:1 (△), 7:2:1 (●), and 4:5:4.5:1 (□) using phosphatidylcholine, cholesterol and stearylamine. For each experiment, tear-induced carboxyfluorescein release was calculated relative to identical liposomes incubated in buffer as indicated in Materials and Methods. Data represent means ± S.E. from at least three independent experiments.

Figure 3:
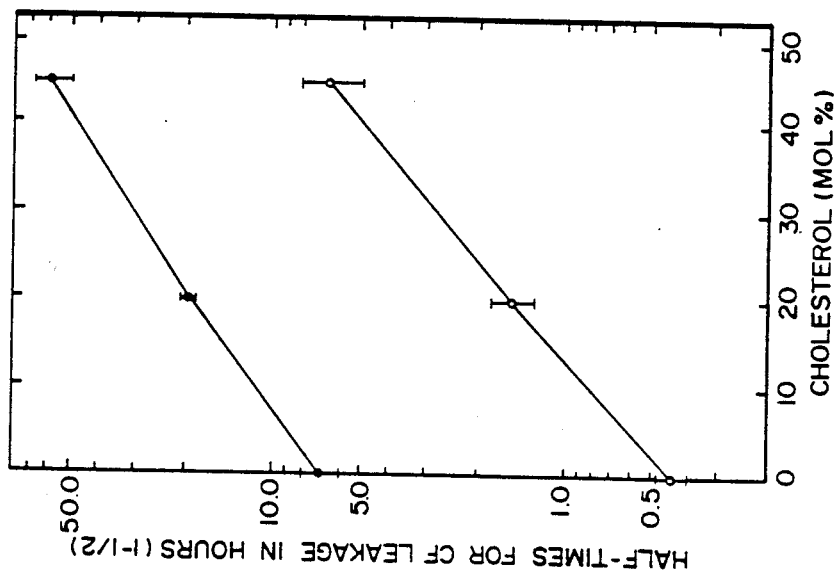
FIG. 3 is a graph illustrating the effect of liposomal cholesterol content on half-times for dye leakage from unilamellar liposomes in the presence of rabbit tear fluid or a buffer.

In FIG. 3, liposomes are incubated in buffer (●) or rabbit rear fluid (○). Data represent means ± S.E. from at least three independent experiments.

Figure 4:
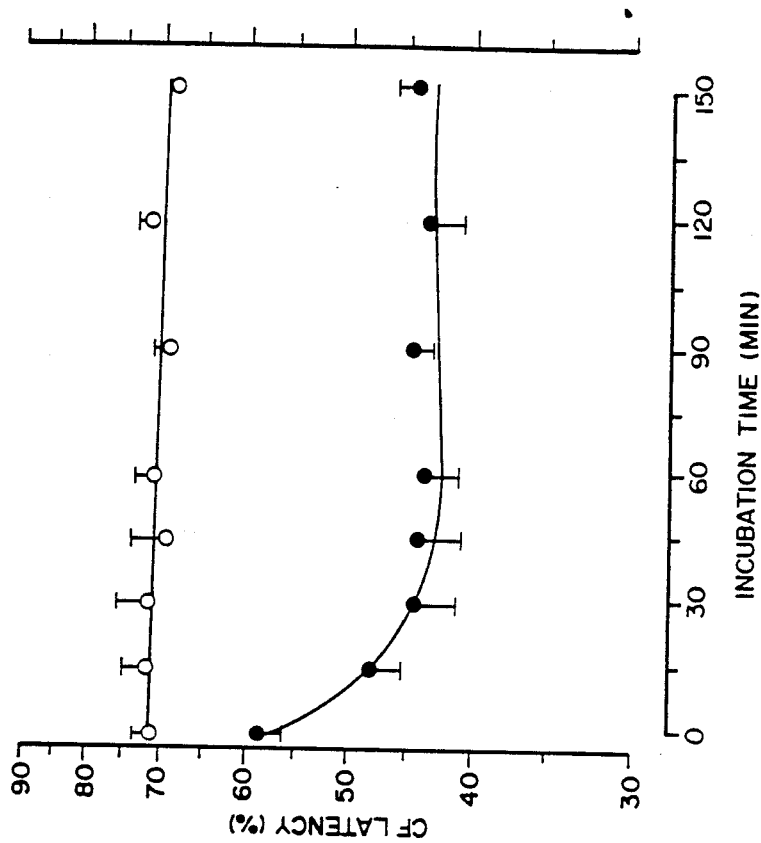
FIG. 4 is a graph illustrating the effect of rabbit tear fluid on marker dye release from multilamellar liposomes.

In FIG. 4, dye-containing multilamellar vesicles (7 egg phosphatidylcholine:2 cholesterol:1 stearylamine) were incubated ar 37° C. in an equal volume of either buffer (○) or tear fluid (◉). Latency values are means ± S.E. from at least three independent experiments.

In a first set of experiments the release of a marker dye, 5-carboxyfluorescein from large unilamellar liposomes (liposome vesciles with only one lipid bilayer or lamellar, enclosing a central aqueous compartment) in the presence of tear fluid was studied in vitro as a function of bilayer cholesterol content. Unilamellar liposomes were used because of their ease of preparation.

While the ability of serum to increase liposome permeability has been reported, little is known about the effect of tear fluid on liposomes. The results presented hereinafter demonstrate that rabbit tears can compromise liposomal integrity as measured by the release of an entrapped marker. Large unilamellar liposomes were prepared from egg phosphatidylcholine, stearylamine and varying amounts of cholesterol. Their stability was monitored by following the release of the marker, the water-soluble, self-quenching fluorescent dye, carboxyfluorescein. Using this method, the half-times for dye release, at all cholesterol levels examined, were approximately 10-times less in the presence of tear fluid than in the presence of Hepes buffer alone.

In the presence of rabbit tear fluid, positively charged (stearylamine-containing) cholesterol-free phosphatidylcholine liposomes rapidly lost most of their entrapped dye within 1 hour. Both the rate (FIG. 3) and the extent of this loss (FIG. 2) could be reduced by incorporating increasing amounts of cholesterol in the liposomal bilayer.

The release of carboxyfluorescein from multilamellar liposomes prepared by the freeze-drying method with a composition of 7 phosphatidylcholine:2 cholesterol:1 stearylamine was also determined (FIG. 4). The release profile for dye from these vesicles is very similar to those observed using unilamellar liposomes (FIG. 1).

Materials and Methods

Animals and tear collection.

The animals used were normal female New Zealand white rabbits, 12–14 weeks old and 2.0–2.5 kg in weight. Tears were collected from the lower eye-lid margins of rabbits with 10 μl micropipettes. Extreme care was taken to avoid irritating the eye so as not to stimulate tearing.

Chemicals.

Egg phosphatidycholine, cholesterol, stearylamine, Hepes and octyl β-D-glucopyranoside were obtained from Sigma (St. Louis, Mo.). 5-Carboxyfluorescein was purchased from Calbiochem-Behring (La Jolla, Calif.) and purity was confirmed by HPLC. All other chemicals were reagent grade.

Preparation of unilamellar liposomes.

Liposomes containing the aqueous dye, carboxyfluorescein, were prepared using the reverse evaporation method according to F. Szoka et al (1978) Proc. Natl. Acad. Sci. USA 75,4194–4198. A total of 66 μmol of lipid, dissolved in organic solvent, was dried onto the side of a pear-shaped flask using a stream of nitrogen. Residual solvent was removed in vacuo for a minimum of 30 minutes. The dried lipid was redissolved in 3 ml of diethyl ether to which 1 ml of 200 mM carboxyfluorescein in 100 mM Hepes (pH 7.4) was added. A stable emulsion was created by sonication at 100 W for 3 minutes using a probe sonicator (Braunsonic 1510). The sample was kept on ice and was purged with nitrogen throughout the procedure. The ether was then removed by rotary evaporation under reduced pressure in a 30° C. waterbath and the resulting vesicles were then either used immediately or stored under nitrogen ar 5° C.

Prior to use, the liposomes were washed twice by ultracentrifugation in 100 mM Hepes (pH 7.4) at 118,000×g for 20 minutes at 5° C. The final pellet was gently resuspended with 0.5 ml of buffer and then passed through a Sephadex G-50 (coarse) column 3.0×25 cm) pre-equilibrated with Hepes buffer. The liposomes were collected in the void volume and used immediately.

Carboxyfluorescein-release assay.

Washed liposomes were mixed with an equal volume of either rabbit tears or Hepes buffer and incubated at 37° C. At specified times, 20-ul aliquots were diluted 5-fold in buffer. A 30-ul aliquot was then mixed with 2 ml of buffer in a cuvette for fluorescence measurements. Fluorescence, before and after the addition of 100 ul of Triton ® x-100 (10%, v/v), was measured using Perkin-Elmer 650-10 M fluorescence spectrophotometer. All measurements were made at room temperature using excitation and emission wavelengths of 488 and 520 nm, respectively, with slit widths of 5 nm.

For each sample, the percent remaining carboxyfluorescein (latency) was calculated by using the fluorescence reading obtained after detergent lysis as 100% efflux. The half-times for carboxyfluorescein leakage were calculated using the initial linear portions of the plots of log[carboxyfluorescein latency] versus time.

Freeze fracture electron microscopy.

Liposome samples were quenched from room temperature by plunging them into partially solidified Freon ®22. No cryoprotectant was used. The samples were freeze-fractured using a Balzers freeze-fracture unit at −100° C. Fractured samples were platinum shadowed at a 45° angle. The carbon replicas were cleaned in concentrated bleach for about 30 minutes and then in chloroform/methanol (2:1, v/v) for a further 10–15 minutes.

Vesicle sizing.

Quasi-elastic light scattering was used to determine the size distribution of the liposome preparation. A small aliquot of sample, prepared without carboxyfluorescein, was diluted to 2 ml with distilled water and light scattering was recorded at an angle of 90° in a thermally jacketed sample chamber maintained at 21.3° C. Measurements were made at three sample times using a helium-neon laser (wavelength 632.8 nm), a quantum photometer, and a 64-channel autocorrelator (Langley-Ford model 1096). Analysis of the resulting autocorrelation functions was carried out using the method of cumulants.

Results

Vesicle morphology and size distribution

Freeze-fracture electron microscopy and light scattering studies revealed that the liposomes prepared by the reverse evaporation method with a molar ratio of 7:2:1 (phosphatidylcholine/cholesterol/stearylamine) were composed almost exclusively of unilamellar vesicles (some oligo- and multilamellar vesicles were observed). These ranged in size from 0.4 to 4.4 μm in diameter. The average vesicle diameter was 1.71 μm. While the other liposome compositions would produce vesicles of different sizes, they should remain essentially unilamellar by virtue of the preparation method used.

Tear-induced release of liposome-entrapped carboxyfluorescein

Carboxyfluorescein-release experiments revealed that, in the presence of rabbit tear fluid, liposomes lacking cholesterol rapidly released most of the entrapped dye with 1 hour (FIG. 1) This tear-induced leakage, however, could be reduced by incorporating cholesterol in the liposomal bilayer.

A comparison of the effects of cholesterol content on tear-induced leakiness is illustrated in FIG. 2. In vesicles prepared with no cholesterol (9:0:1), 80% more dye was released within the first hour, relative to the controls, with a greatly reduced, but continued, rate of release thereafter. Liposomes prepared with equimolar amounts of phosphatidylcholine and cholesterol (4.5:4.5:1) were still susceptible to tear-induced leakiness; however, the average amount of dye released was reduced to less than 19% of controls during the 5 h course of the experiment. At the intermediate composition (7:2:1), tear-induced dye release was still pronounced, but gradual, with 41.5% more dye being released at 1 h. This release increased to 65.7% after 5 h.

Half-times for carboxyfluorescein leakage

The half-times for carboxyfluorescein release, calculated using first-order kinetics, are shown in FIG. 3 and are approximately one order of magnitude less in the presence of tear fluid. Preparations incubated only in Hepes buffer showed an expected increase in half-times rising from 7.0 to 60.5 h as the proportion of cholesterol was increased from 0 to 45 mol%. The ability of cholesterol to protect the vesicles against tear-induced release is reflected by the roughly parallel increase in half-times observed in the presence of tear fluid. Using the 9:0:1 1 vesicle composition, the half-time for carboxyfluorescein release was 0.43 h. This increased to 6.6 h at the highest cholesterol content used, i.e. 45 mol%.

In another set of experiments, the use of slow-sustained release property of the novel liposomes according to the invention was studied. For this study, the liposomes employed were multilamellar liposomes (i.e. liposomes having multiple bilayers) comprising egg phospholipid, cholesterol and stearylamine or phosphatidic acid in various combinations. Multilamellar liposomes were used in all in vivo testing since they provide a better possibility of slow sustained release of entrapped prophylactic agent than unilamellar liposomes.

A number of methods are available for the preparation of different types of liposomes. Applicant employed the freeze-drying technique according to C. J. Kirby et al in Liposome Technology, Vol. 1, 19–27, CRC Press. Boca Raton, 1984. Thus, freeze-dried multilamellar vesicles (FDV) were used for the entrapment of acetylcholinesterase (AChE) The freeze-drying method was chosen because of its simplicity and more importantly, because during preparation, the enzyme is at no time exposed to organic solvents, detergents, or sonic energy, all of which have been found to destroy the enzyme's activity completely. Thus, most of the commonly used liposome-preparation procedures, e.g., reverse-phase evaporation, solvent-injection, and detergent-dialysis methods, are inappropriate. Another advantage of the freeze-drying method is that FDV can be stored and are easily reconstituted. Samples stored under an atmosphere of nitrogen at −20° C. or as long as 7 months still retained 75% of their original enzyme activity. The practical usefulness of most liposome preparations of ocular applications appears to be limited by their inherent short shelf-life. Therefore, the relatively long period of stability of enzyme-containing FDV upon storage becomes another added advantage.

In addition, the multilamellar nature of the liposomes prepared by the freeze-drying technique is deemed desirable for a more gradual and sustained release of the entrapped AChE for prolonged prophylactic periods. The size-frequency distribution of the AChE-containing FDV indicates the presence of vesicles ranging in diameter from about 0.2 to 4 μm. The predominant FDV population, however, is between 0.6–1.8 μm and the average diameter of all the vesicles is 1.7 μm.

Specifically, a total of 66 μmol of lipids dissolved in chloroform/methanol (2:1 v/v) were dried in a thin film on the bottom of a screw-capped culture tube with a stream of nitrogen. Egg phosphatidylcholine, cholesterol, and stearylamine or phosphatidic acid were used in various combinations (7–8:2:0–1). Egg phosphatidylcholine is employed because of its relatively low transition temperature (below 0° C.) and the added convenience of allowing preparation of the liposome product at room temperature. Higher temperatures and thermal regulation are required for the preparation of liposomes using other lipids with high transition temperatures. The lipids were further dried in vacuo for 30 min after which they were hydrated with 1 ml of 4 mM $NaHCO_3$, pH 7.4. The samples were then vigorously vortexed at room temperature (20° C.) prior to the addition of 1 ml of AChE (type V-S, Sigma) dissolved in distilled water at 2 mg/ml. After mixing, the samples were shell frozen and then freeze-dried overnight. On the day before use, the samples were rehydrated with 200 μl of distilled water at 5° C. overnight. The reconstituted liposomes were then washed twice by pelleting in 38 ml of 4 mM $NaHCO_3$ at 10,000×g for 20 min. The final pellet was taken up to 1 ml in 4 mM $NaHCO_3$, pH 7.4 and enzyme activity was determined colorimetrically using a cholinestarase diagnostic kit (Sigma kit no. 420).

For freeze-fracture electron microscopy, samples were quenched from room temperature by plunging into partially solidified Freon®22. The samples were freeze-fractured using a Balzers freeze-fracture unit at −100° C. Fractured samples were platinum shadowed at an angle of 45°. The carbon replicas were cleaned in concentrated bleach for about 30 min and then in chloroform/methanol (2:1 v/v) for a further 10–15 min. The replicas were examined using a Philips model 300 transmission electron microscope.

Vesicle sizing was done by quasi-electric light scattering. A small aliquot of sample was diluted to 2 ml with distilled water and light scattering was recorded at an angle of 90° in a thermally jacketed sample-chamber maintained at 21.3° C. using a helium-neon laser (wavelength 632.8 nm), a quantum photometer and a 64-channel autocorrelator (Langley-Ford model 1096). Measurements were made at 3 sample times and analysis of the resulting autocorrelation functions was carried out using the method of cumulants.

We used an extremely sensitive biological test involving the induction of miosis by DFP to determine whether liposomes may serve as an effective carrier system for the delivery of prophylactic agents in the eye. Instead of using atropine, a commonly-used drug for preventing miosis, which unfortunately also causes mydriasis, we used AChE as the prophylactic agent. AChE binds irreversibly to DFP which interacts chemically with a serine hydroxyl group in the enzyme active site. The rationale in using liposomes as the prophylactic carrier is at least two-fold. Firstly, the liposome vesicles may be less susceptible to wash-out by tear flow and, secondly, if the slow release of entrapped materials is required, liposome may achieve a longer prophylactic period. Additionally, if multilamellar liposomes are employed an even longer release period should be attained.

Two experiments were performed to illustrate the efficacy of FDV-encapsulated AChE in counteracting DFP-induced miosis. The animals used were normal female New Zealand white rabbits, 12-14 weeks old and 2.0-2.5 kg in weight. Each animal to be examined was gently hand-restrained on a table and the eye was illuminated at 2.5 mWatt/cm$^2$ by a rheostare-controlled incandescent light placed at a distance of 0.5 m away. Measurements of the pupil size were made as follows: A mm-scale was positioned below the lower eye-lid and photographs were taken with a Nikormat single-lens-reflex camera fitted with a 135-mm lens and loaded with Kodak Ektachrome film (ASA 200). The aperture setting was F/5.6 at a shutter speed of 1 sec. Data on the pupil size were determined by projection of the slides on a screen and measurements were made using the projected mm-scale accompanying the picture of each eye. Determinations of the pupil size, comparable in accuracy to the photographic method, are also possible by a direct measurement of the pupil using a hand-held mm-ruler. The baseline pupil size was first determined prior to any treatment applied to the eye.

In a first experiment, liposome-entrapped AChE, possessing 144 Rappaport units RU, 18) of enzyme activity, was applied to one eye of the rabbit 2 h before the instillation of DFP. The contralateral eye of the same animal served as the control and received a identical dose of AChE, but in free form. The effective dose of DFP applied to induce a reduction of the pupil size by 50% was predetermined to be 4 ug (ED$_{50}$). Thus, it can be seen from FIG. 5 that Pretreatment with liposome-entrapped AChE signifantly reduced DFP-induced miosis. On the other hand, the application of free AChE solution or plain liposomes did not provide any protection against a similar DFP challenge.

Specifically, pretreatment consisted of administering to the eye either enzyme-containing liposomes (AChE-FDV), free enzyme (AChE), or plain liposomes (FDV). The dose of AChE applied in each case contained 140 RU of enzyme activity and the lipid content of the FDV (7PC:2CSL:1SA) applied was 2.6 μmol. The topical application was performed by dropping the appropriate preparation (40 μl) on the cornea with the excess retained by the conjunctival sac. Two h later, each eye was subjected to a miotic challenge by the instillation of an effective dose (4 μg in 20 μl) of DFP previously determined to reduce the pupil size by 50% (ED$_{50}$). Subsequent changes in the pupil size were monitored at hourly intervals. Each point in FIG. 5 represents the mean percentage of original pupil size ± SEM of the number of determinations indicated.

We also compared the effectiveness of a wide dose range of liposome-entrapped AChE in counteracting -DFP-induced miosis. At a dose range between 40 and 400 RU, the extent of protection afforded by FDV-AChE remained essentially the same and the pupil size was maintained at about 85%. When the dose of liposome-entrapped enzyme was lowered to 20 RU, the pupil size was reduced to about 65% upon challenge by DFP at ED$_{50}$.

In addition to a minimal dose of entrapped AChE which is required for a significant prophylactic effect, the surface charge of the lipid vesicle also appears to be important. In FIG. 6, positively charged vesicles (7PC:2CSL:1SA) provided the best prophylactic effect compared with either neutral 8PC:2CSL) or negatively charged (7PC:2CSL:1PA) vesicles. The reason for this difference is not clear. Because the corneal epithelium is thinly coated with negatively charged mucin, the positive surface charge of the liposome may provide for a more stable adsorption to the corneal surface. The enhanced adhesion of positive liposomes to the corneal surface may also be a factor.

Specifically, the effectiveness of AChE-containing liposomes of different surface charge in preventing DFP-induced miosis was determined. The pretreatment of the eye consisted of the instillation of either (a) free AChE solution, (b) AChE encapsulated in neutral FDV 8PC:2CSL), (c) AChE in negatively charged FDV (7PC:2CSL:1PA), or (d) AChE in positively charged FDV 7PC:2CSL:1SA). The dose of AChE applied to each eye was between 140 to 144 RU of enzyme activity and the FDV lipid content was 2.6 μmol. Two h after pretreatment, each eye was challenged with an ED$_{50}$ of DFP. Each vertical bar in FIG. 6 represents the mean percentage of original pupil size ± SEM of the number of determinations indicated in the figure. Comparison of the statistical significance (Student's t-test) between the mean values among different groups: a and b, $p<0.02$; a and c, $p<0.05$: a and d, $p<0.0001$; b and c, n.s.; b and d, $p<0.0001$; c and d, $p<0.003$. (Abbreviations for lipids: CSL, cholesterol; PA, phosphatidic acid; PC, phosphatidylcholine; SA, stearylamine.)

Thus, applicant has demonstrated that liposomes according to the invention can serve as an effective carrier for the topical ocular delivery of a prophylactic enzyme in counteracting chemical-induced miosis. The effectiveness of the enzyme-containing liposome appears to stem from its ability in mopping up the miotic agent and in releasing the entrapped enzyme to neutralize the agent's toxic action. Unlike other studies in which liposomes were used to facilitate the corneal penetration of entrapped drugs, the rationale of our current approach is to utilize liposomes to prolong the ocular contact time of a prophylactic agent. Therefore, the ocular penetration of the entrapped prophylactic agent is not a prerequisite for successful prophylaxis. The released enzyme simply acts as a neutralizing barrier which counteracts the insult of the invading toxic agent.

An exciting potential is the use of this approach for preventing and alleviating the irritating ocular symptoms of certain allergy sufferers to air-borne allergens.

It will be appreciated by those skilled in the art that although acetylcholinesterase is the only prophylactic agent exemplified, many other such agents including drugs and biologically active materials which gain entry to ocular tissues may also be successfully employed.

The embodiments of the invention in which an exclusive property or privilege is claimed are defined as follows:

1. A method for the ocular delivery of a prophylactic agent, which comprises applying to the eye a liposome containing the prophylactic agent, wherein the liposome composition comprises phospholipid and cholesterol in a molar ratio of phospholipid to cholesterol of 8:2 to 1:1 with the prophylactic agent entrapped therein.

2. A method according to claim 1, wherein the phospholipid is phosphatidylcholine.

3. A method according to claim 2, wherein the phosphatidylcholine is egg phosphatidylcholine.

4. A method according to claim 3, wherein the prophylactic agent is acetylcholinesterase.

5. A method according to claim 4, wherein the composition is in the form of a multilamellar liposome vesicle.

6. A method for the slow-sustained ocular release of a prophylactic agent which comprises applying to the eye a liposome containing the prophylactic agent, wherein the liposome composition comprises phospholipid, cholesterol and stearylamine in a molar ratio of phospholipid, cholesterol and stearylamine of 4.5–9:0-.5–4.5:1.

7. A method according to claim 6, wherein the molar ratio of phospholipid to cholesterol to stearylamine is about 7:2:1.

8. A method according to claim 7, wherein the phospholipid is phosphatidylcholine.

9. A method according to claim 8, wherein the phospholipid is egg phosphatidylcholine.

10. A method according to claim 1 or 9, wherein the composition is in the form of a multilamellar liposome vesicle.

11. A method according to claim 1 or 9, wherein the prophylactic agent is acetylcholinesterase.

12. A method of protecting the eyes from invading toxic agents to which they are exposed comprising instilling in the eyes a protective amount of a liposome composition in which the liposome carries and prolongs the ocular contact time of a prophylactic agent, the liposome composition consisting essentially of (a) phospholipid and cholesterol in a molar ratio of phospholipid to cholesterol of 8:2 to 1:1, or (b) phospholipid, cholesterol and stearylamine in a molar ratio of phospholipid to cholesterol to stearylamine of 4.5–9:0-.5–4.5:1.

13. The method of claim 12 in which the toxic agent is a miotic agent and the prophylactic agent is an enzyme that neutralizes the miotic agent.

14. A method of preventing or alleviating irritating ocular symptoms caused by air-borne allergens comprising applying to the eyes of a person exposed to air-borne allergens a liposome containing a prophylactic agent, wherein the liposome composition comprises phospholipid and cholesterol in a molar ratio of phospholipid to cholesterol of 8:2 to 1:1 with the prophylactic agent entrapped in the liposome or phospholipid, cholesterol and stearylamine in a molar ratio of phospholipid to cholesterol to stearylamine of 4.5–9.0:0-.5–4.5:1.

* * * * *